(12) United States Patent
Cummings

(10) Patent No.: US 7,727,402 B2
(45) Date of Patent: Jun. 1, 2010

(54) DUAL-CHAMBER CHROMATOGRAPHIC CARTRIDGE

(75) Inventor: Larry J. Cummings, Pleasant Hill, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 867 days.

(21) Appl. No.: 11/560,592

(22) Filed: Nov. 16, 2006

(65) Prior Publication Data

US 2007/0114163 A1     May 24, 2007

Related U.S. Application Data

(62) Division of application No. 11/059,177, filed on Feb. 15, 2005, now Pat. No. 7,208,087.

(51) Int. Cl.
*B01D 15/08* (2006.01)
(52) U.S. Cl. ............... 210/656; 210/198.2; 210/282; 141/12; 141/80
(58) Field of Classification Search ............. 210/635, 210/656, 659, 198.2, 282, 285, 286, 288; 141/12, 80
See application file for complete search history.

(56) References Cited

U.S. PATENT DOCUMENTS

| | | | |
|---|---|---|---|
| 2,891,630 A | 6/1959 | Hall et al. | |
| 4,451,363 A * | 5/1984 | Brownlee et al. | 210/198.2 |
| 4,565,632 A | 1/1986 | Hatch et al. | |
| 4,676,898 A | 6/1987 | Saxena | |
| 4,968,421 A * | 11/1990 | Spacek et al. | 210/198.2 |
| 5,124,023 A * | 6/1992 | Bosserman et al. | 208/99 |
| 5,582,723 A | 12/1996 | Boon et al. | |
| 5,601,708 A | 2/1997 | Leavesley | |
| 5,863,428 A | 1/1999 | Ma et al. | |
| 6,001,253 A | 12/1999 | Conroy et al. | |
| 6,068,766 A | 5/2000 | Van Davelaar | |
| 6,117,329 A | 9/2000 | Hargro | |
| 6,132,605 A | 10/2000 | Leavesley et al. | |
| 6,171,486 B1 | 1/2001 | Green et al. | |
| 6,177,008 B1 | 1/2001 | Treiber et al. | |
| 6,398,953 B1 | 6/2002 | Hargro | |
| 6,444,122 B1 | 9/2002 | Van Davelaar | |

FOREIGN PATENT DOCUMENTS

| | | |
|---|---|---|
| GB | 585224 | 2/1947 |
| JP | 2001-318087 A | 11/2001 |
| WO | WO 95/27547 A1 | 10/1995 |

* cited by examiner

*Primary Examiner*—Ernest G Therkorn
(74) *Attorney, Agent, or Firm*—Townsend and Townsend and Crew LLP.; M. Henry Heines

(57) ABSTRACT

A chromatography cartridge with a packed bed is manufactured from an inner and outer chamber, the inner chamber being in an insert that is slidable into the outer chamber with openings in each such that a slurry that is originally placed in the interior of the outer chamber flows into the inner chamber as the parts are being pressed into each other. During the assembly, the particles in the slurry are compressed to fill the smaller volume of the inner chamber and excess liquid is discharged through ports in both chambers. The construction allows for a highly precise and reproducible column filling process with a minimum of steps and operator intervention and thereby low cost and reduced error.

6 Claims, 3 Drawing Sheets

DUAL-CHAMBER CHROMATOGRAPHIC CARTRIDGE

CROSS-REFERENCE TO RELATED APPLICATION

This application is a division of U.S. patent application Ser. No. 11/059,177, filed Feb. 15, 2005, now U.S. Pat. No. 7,208, 087, the contents of which are incorporated herein by reference in their entirety.

BACKGROUND OF THE INVENTION

1. Field of the Invention

This invention resides in the field of laboratory apparatus for chromatographic separations of liquid samples. This invention is particularly concerned with packed-bed column cartridges and their method of manufacture.

2. Description of the Prior Art

Packed-column chromatography is widely used in clinical laboratories and research laboratories by virtue of its ability to separate components of liquid samples from many sources and for many reasons. As both an analytical tool and a diagnostic tool, packed-column chromatography offers a means of providing rapid determinations with a minimum of effort and sample preparation. As in all analytical and diagnostic methods, the value of packed-column chromatography is greatest when a large number of samples are to be analyzed under the same criteria or for comparison with each other or with a standard. The optimal packed-column chromatography system is therefore one that produces separations quickly and in a reproducible and reliable manner. This requires standardized conditions which include a high degree of control over the packing volume, the packing density and the flow pattern of the sample and carrier liquid through the packing. These qualities are all enhanced when there is minimal opportunity for user error.

The need for speed, uniformity and reliability has led to the development of column cartridges or pre-packaged disposable columns, which are manufactured by mass production, purchased in bulk, and used either once or a limited number of times before being discarded. The use of cartridges that are packed by the manufacturer sharply reduces the opportunity for user error, and offers the standardization and uniformity that comes with high-volume manufacture and mass production techniques. Nevertheless, prepackaging shifts the error to the manufacturing process, where opportunities for error and variability still exist. Such factors as the inattentiveness of individuals in the manufacturing plant and changes of manufacturing personnel can introduce nonuniformities into the product, and in any event, the cost of labor remains a factor, particularly when a precision product is sought.

SUMMARY OF THE INVENTION

The present invention resides in a dual-chamber chromatography cartridge in which an outer chamber is designed to allow sliding entry of an inner chamber having an open end and a smaller volumetric capacity than the outer chamber, and one or both of the chambers has a liquid discharge port that allows passage of liquid while blocking passage of solid particles. The cartridge is thus packed and assembled by charging the outer chamber with a slurry of solid particulate packing material in a carrier liquid, then inserting the inner chamber into the outer chamber and sliding the inner chamber into the full depth of the outer chamber to force the slurry into the interior of the inner chamber while compressing the particulate material within the inner chamber. By selecting a volume of slurry that contains sufficient particulate material to fill the interior of the inner chamber when the particulate material is packed and no more, and by allowing any excess carrier liquid to escape through the discharge port while the particulate material is being packed, the inner chamber upon full insertion will be densely packed with the particulate material in a uniform and highly controlled manner by two simple steps—charging the outer chamber with the slurry and inserting the inner chamber to its full depth. This reduces the number of steps in the packing process, allows the use of automated packing procedures with precisely controlled pressures, flow rates, and other operating conditions, and results in a finished cartridge that is ready to use with a high degree of user confidence and reliability and low cost. The present invention thus resides in a process for manufacturing a packed-bed chromatography cartridge utilizing the inner and outer chambers and a slurry of the packing material, and in the combination of components that constitute the cartridge. Further objects, features, and advantages of the invention will be apparent from the description that follows.

DETAILED DESCRIPTION OF THE INVENTION AND PREFERRED EMBODIMENTS

Figure 1:
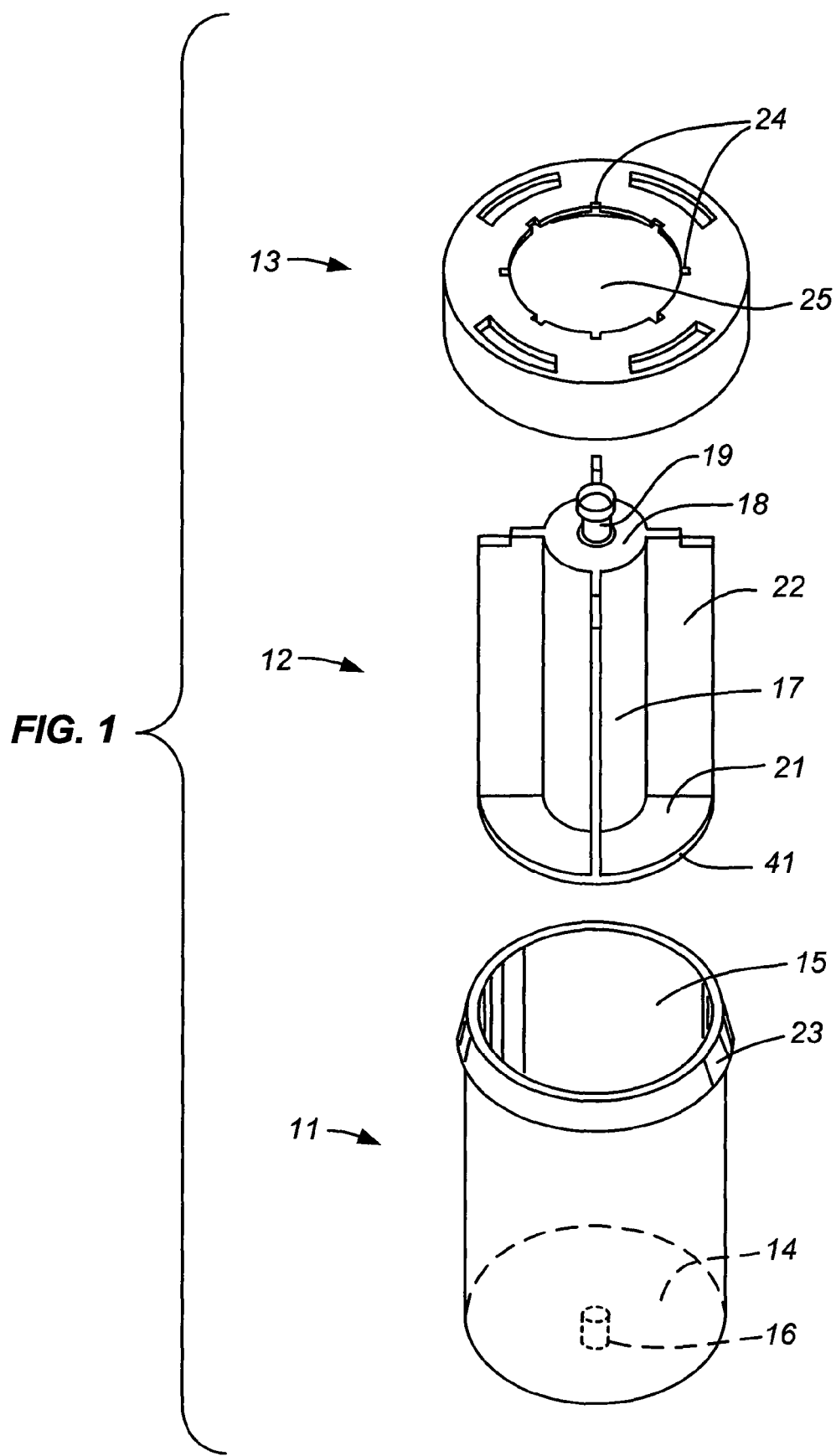
FIG. 1 is a perspective view of the components of a cartridge in accordance with the present invention.

The inner and outer chambers of the cartridges of this invention can vary widely in size and configuration, although preferably both are cylindrical with circular cross sections. The inner chamber will be selected with an axial length and cross-sectional area that are suitable for the chromatographic separations to be performed in the cartridge. These dimensions will therefore vary according to the size of the sample to be separated or analyzed, the particle size and volume of the packing material, and any other parameters of the separation, and it will be beneficial for a supplier to offer a range of sizes. The ratio of the cross-sectional area of the interior of the inner chamber to that of the interior of the outer chamber can for example range from about 0.05 to about 0.5. The volume of the inner chamber, and hence the bulk volume of the separation medium in the finished cartridge, can for example range from about 0.5 mL to about 50 mL, or preferably from about 1 mL to about 25 mL. Likewise, the length of the inner chamber can for example range from about 1.0 cm to about 20 cm, or preferably from about 3 cm to about 10 cm, and the length-to-diameter ratio of the interior of the inner chamber can for example range from about 1.25 to about 25, or preferably from about 1.4 to about 10. In preferred embodiments of the invention, the inner and outer chambers are of equal or approximately equal length.

The packing material is supplied as a slurry to facilitate the placement of the material in the outer cylinder and also to facilitate the passage of the material from the outer cylinder into the inner cylinder as the two cylinders are pressed together. The slurry will contain an excess of carrier liquid to improve the flowability of the particles, and the excess liquid will be discharged as the particles are compressed into a packed bed. The volume of the slurry when first placed in the interior of the outer cylinder will thus be greater than the volume of the interior of the inner cylinder and likewise greater than the final volume of the packed bed. The slurry volume may for example be about 120% or more of the final packing volume, preferably about 150% or more, and most preferably about 200% or more. The outer chamber will be sized to accommodate this slurry volume, preferably with excess space so that the slurry will occupy only a portion of the outer chamber. A precisely determined volume of slurry can then be added, and the volume adjusted as needed for different quantities of carrier liquid relative to the suspended particles. The same outer cylinder can be used with inner cylinders of different sizes and hence different slurry and particle volumes.

The particles that form the packed bed are referred to herein as "solid." This term is used in the present specification and claims to include both rigid particles and deformable resilient particles, and in general any particles that are known to be useful as a stationary phase for chromatographic separations. The term "packing volume" is used herein to denote the bulk volume occupied by a mass of particles that has been compressed to full packing density, i.e., to the point where the particles are in full contact and not movable either by agitation or by the flow of liquid across the bed. The remaining carrier liquid will occupy the interstitial spaces between the packed particles.

As the slurry is compressed and the particles packed, excess carrier liquid is discharged through a discharge port in one or both of the chambers. Preferably, the inner chamber has a discharge port, and most preferably, both the inner and outer chambers have discharge ports. When two ports are present, they will serve as inlet and outlet ports, respectively, for the elution buffer in a chromatographic separation as the separation is being performed in the packed cartridge. The port, or ports when two are present, are configured to allow the passage of carrier liquid but to block the passage of the particles, thereby allowing the particles to pack to full packing density while the chamber cylinders are pressed together and the excess liquid is being discharged. To thus retain the particles while passing the liquid, the ports will be either substantially smaller than the particles or will contain particle blocking members such as frits, filters, mesh disks, and the like. The frits, filters or disks can reside inside the ports themselves or can be placed over the port openings.

While the invention is susceptible of a variety of physical configurations, the novel features of the invention that are common to all such configurations can be understood by a detailed review of one example. Such an example is shown in the attached drawings and described below.

The perspective view of FIG. 1 shows three components of an illustrative cartridge, the components spatially separated for ease of viewing. The components include a cylinder 11, an insert 12, and an end cap 13. The cylinder 11 is closed by a floor 14 at the bottom and open at the top 15, with a discharge port 16 extending downward from the floor. The interior of the cylinder 11 serves as the outer chamber of the cartridge. The insert 12 includes a smaller cylinder 17 whose interior serves as the inner chamber of the cartridge. The smaller cylinder 17 has an open bottom (not visible in this Figure) and a roof or top 18 that is closed except for a discharge port 19 at its center and extending upward. Both the lower discharge port 16 and the upper discharge port 19 in this embodiment are shaped as components of LUER-LOK® fittings, although any connective fittings can be used that are designed to provide fluid-tight connections to transfer tubing or to other ports in a full chromatographic apparatus. The insert has a base flange 21 and centering ribs 22 symmetrically arranged around the smaller cylinder 17 to center the smaller cylinder inside the larger cylinder 11. The end cap 13 secures the insert inside the larger cylinder 11 by pressing against the upper edges of the centering rubs 22 and engaging, i.e., hooking over, a skirt 23 at the top of the larger cylinder 11 that encircles the outer side of the opening 15. Notches 24 in the inner rim of a central opening 25 of the end cap engage the outer corners of shoulders 26 in the centering ribs of the insert for further securement and stabilization.

Figure 2:
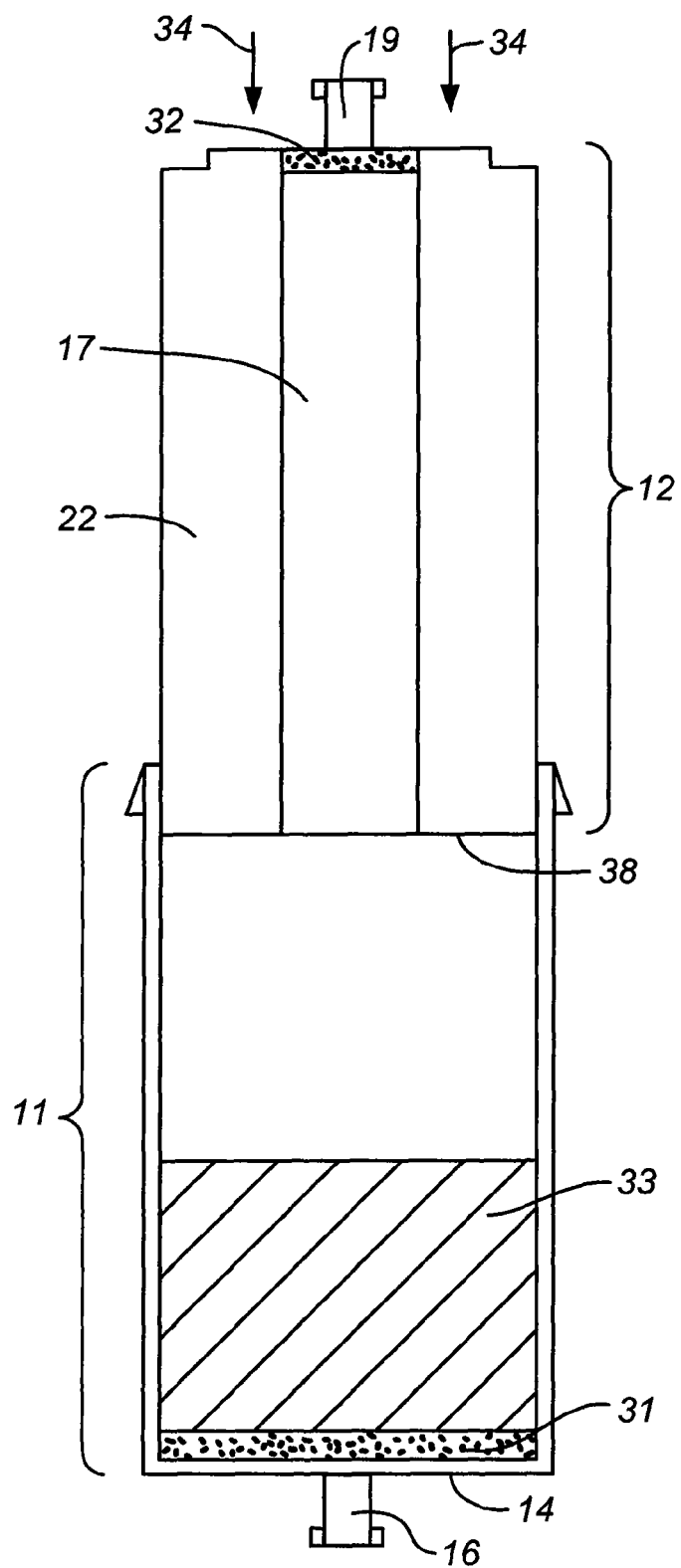
FIG. 2 is a cross section of two of the three components of FIG. 1 in partially assembled configuration.
Figure 3:
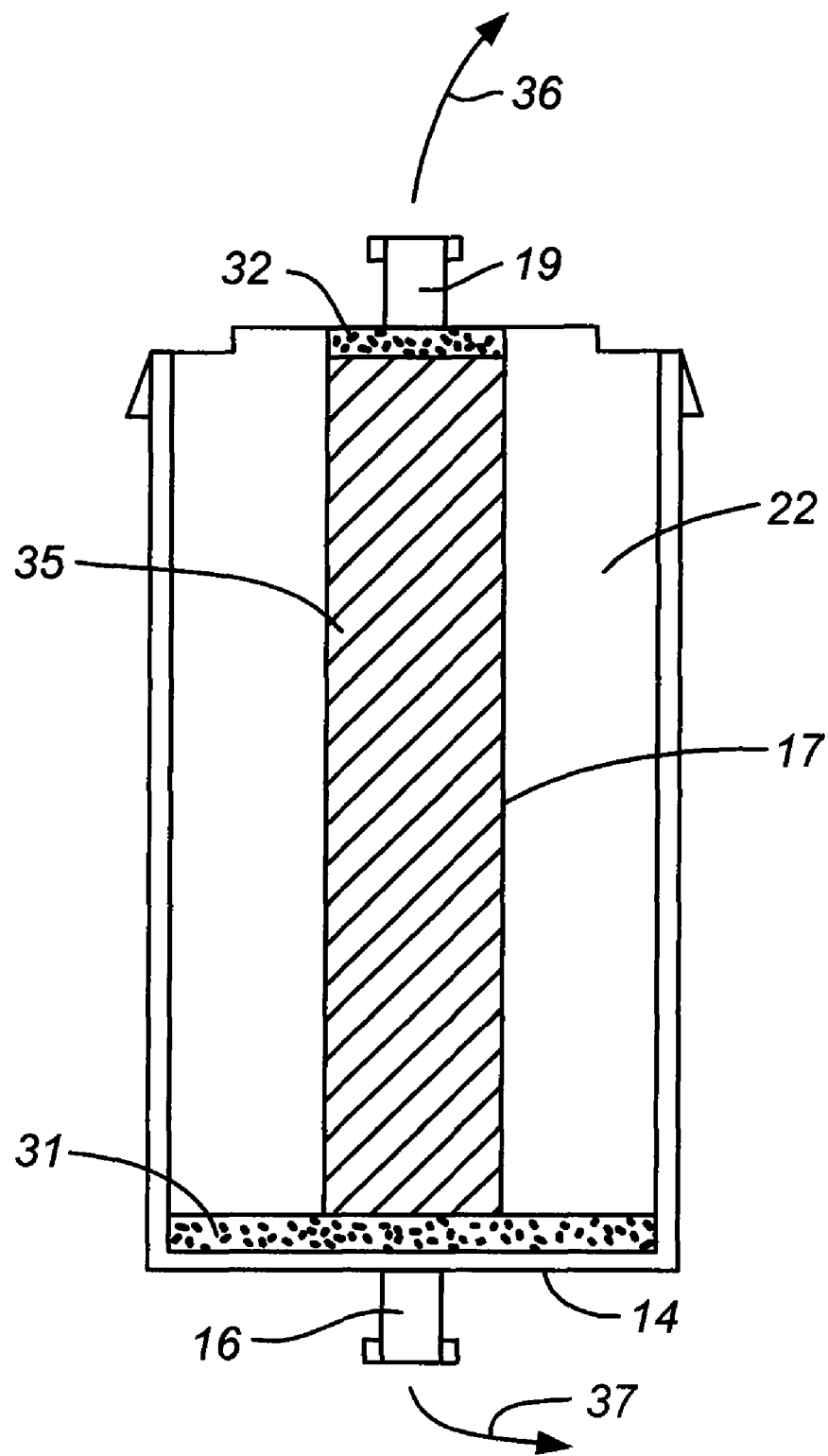
FIG. 3 is a cross section of the same components as FIG. 2 except fully assembled.

The axial cross sections of FIGS. 2 and 3 show the larger cylinder 11 and the insert 12, both taken along the aligned centerlines of each and in the planes of two opposing centering ribs 22. The end cap 13 is not shown in these Figures. Both Figures do however show two frits, one 31 on the floor of the larger cylinder to block the entry of particles into the lower discharge port 16 from the interior of the larger cylinder 11, and the other 32 placed inside the interior of the smaller cylinder 17 of the insert 12 where it blocks the entry of particles to the upper discharge port 19 from the interior of the smaller cylinder 17. In the view shown in FIG. 2, a volume of slurry 33 has been placed in the larger cylinder 11, in the which the discharge port 16 is closed with a male LUER-LOK® cap, followed by placement of the insert 12 a short distance into the interior of the larger cylinder 11 with the open ends of both cylinders facing each other. The insert 12 is then pushed downward into the larger cylinder 11 applying pressure to the upper end of the insert as indicated by the arrows 34, and the slurry is forced into the interior of the smaller cylinder 17 of the insert 12.

The resulting configuration is shown in FIG. 3 in which particles of the slurry have been retained inside the interior of the smaller cylinder 17 where they form a packed bed 35. The packed bed 35 is smaller in volume than the slurry, since it contains the particles fully packed, with excess carrier liquid having been expelled through the discharge port 16 as indicated by the arrow 36.

Both solid particles and carrier liquid are prevented from entering the annular space between the two cylinders and between the centering ribs 22 by the base flange 21. This flange is visible in FIGS. 2 and 3 only by its lower surface 38, since these Figures are cross sections taken through a plane that includes the centering ribs. The base flange 21 is more readily visible in FIG. 1, where the outer edge 41 of the base flange is visible. This outer edge forms a sliding fluid-tight seal against the inner wall of the interior of the larger cylinder 11 to prevent passage of both liquid and solid. To facilitate the seal while allowing the insert to be slid into place, the flange or the entire insert can be manufactured from a material that is relatively rigid compared to the larger cylinder 11. The relatively soft larger cylinder will thus be slightly deformed during insertion of the insert by the outward pressing force of the flange edge 41 against the cylinder wall.

The foregoing is offered for purposes of illustration. Further variations, modifications, and substitutions that fall within the scope of the invention will be readily apparent to those skilled in the art.

What is claimed is:

1. A process for the manufacture of a chromatography cartridge containing a selected volume of solid particulate packing material at a selected packing volume, said process comprising:
   (a) charging a first chamber with a slurry of said solid particulate packing material in a carrier liquid, the packing material in said slurry being of a quantity that when fully packed fills said selected packing volume, said first chamber having a longitudinal axis, an open first end, and a second end containing a liquid discharge port adapted to allow passage of liquid while blocking passage of said solid particles, (b) joining a second chamber to said first chamber, said second chamber having an open first end, a second end containing a vent port adapted to allow passage of liquid while blocking passage of said solid particles, and an internal cavity having a volume equal to said selected volume of solid particulate packing material, by inserting said open first end of said second chamber into said open first end of said first chamber, and (c) sliding said second chamber further into said first chamber, thereby forcing substantially all of said solid particulate matter plus at least a portion of said carrier liquid into said second chamber through said open end of said second chamber while compressing said particulate matter in said second chamber to said packing volume and discharging excess carrier liquid through said liquid discharge port, said vent port, or both.

2. The process of claim 1 wherein said slurry of step (a) contains sufficient carrier liquid that the volume of said slurry is greater than or equal to 120% of said selected packing volume.

3. The process of claim 1 wherein said slurry of step (a) contains sufficient carrier liquid that the volume of said slurry is greater than or equal to 150% of said selected packing volume.

4. The process of claim 1 wherein said slurry of step (a) contains sufficient carrier liquid that the volume of said slurry is greater than or equal to 200% of said selected packing volume.

5. The process of claim 1 wherein said first and second chambers are of substantially equal length.

6. The process of claim 1 wherein the ratio of cross sectional areas of said second chamber to said first chamber is from about 0.05 to about 0.5.

\* \* \* \* \*